United States Patent
Russell et al.

(10) Patent No.: US 8,429,783 B2
(45) Date of Patent: Apr. 30, 2013

(54) LIGHT-EMITTING ORAL CARE IMPLEMENT

(75) Inventors: Bruce M. Russell, Howell, NJ (US); James H. Kemp, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 1361 days.

(21) Appl. No.: 12/093,686

(22) PCT Filed: Nov. 14, 2006

(86) PCT No.: PCT/US2006/060875
§ 371 (c)(1),
(2), (4) Date: May 14, 2008

(87) PCT Pub. No.: WO2007/111703
PCT Pub. Date: Oct. 4, 2007

(65) Prior Publication Data
US 2008/0276393 A1 Nov. 13, 2008

Related U.S. Application Data

(60) Provisional application No. 60/736,250, filed on Nov. 14, 2005.

(51) Int. Cl.
*A46B 15/00* (2006.01)
(52) U.S. Cl.
USPC ................................ 15/105; 15/167.1; 300/21
(58) Field of Classification Search ............ 15/105, 15/167.1; 300/21; *A46B 15/00*
See application file for complete search history.

(56) References Cited

U.S. PATENT DOCUMENTS

| | | | |
|---|---|---|---|
| 2,688,971 | A | 9/1954 | Daniels et al. |
| 3,261,978 | A | 7/1966 | Brenman |
| 6,026,828 | A | 2/2000 | Altshuler |
| 6,149,288 | A | 11/2000 | Huang |
| 6,406,099 | B2 | 6/2002 | Boucherie |
| 6,702,394 | B2 | 3/2004 | Boucherie |
| 6,752,627 | B2 | 6/2004 | Lin |
| 6,779,851 | B2 | 8/2004 | Bouchiere |
| 6,862,771 | B1 | 3/2005 | Muller |
| 6,905,176 | B2 | 6/2005 | Boucherie |
| 7,143,462 | B2 | 12/2006 | Hohlbein |

(Continued)

FOREIGN PATENT DOCUMENTS

| | | |
|---|---|---|
| CN | 1333660 A | 1/2002 |
| CN | 2574486 Y | 9/2003 |

(Continued)

OTHER PUBLICATIONS

International Search Report and Written Opinion in International Application No. PCT/US06/060875, mailed Oct. 17, 2007.

*Primary Examiner* — Monica Carter
*Assistant Examiner* — Stephanie N Berry

(57) ABSTRACT

An oral care implement comprises a head with a plurality of cleaning elements, and a light source incorporated into or adjacent the head. The light source is incorporated prior to the attachment of the cleaning elements. For ease of manufacturing and a cost-effective assembly. The cleaning elements are preferably preformed and attached to the head after the incorporation of the light source so that the provision of the light source does not require any post-processing that might impair the integrity of the head or cleaning elements.

21 Claims, 12 Drawing Sheets

U.S. PATENT DOCUMENTS

| | | | |
|---|---|---|---|
| 2003/0076281 A1* | 4/2003 | Morgan et al. | 345/44 |
| 2004/0019990 A1 | 2/2004 | Farrell et al. | |
| 2004/0053190 A1* | 3/2004 | Lin | 433/29 |
| 2004/0193235 A1 | 9/2004 | Altshuler et al. | |
| 2005/0066459 A1 | 3/2005 | Pinyayev et al. | |
| 2005/0255416 A1 | 11/2005 | Haase | |
| 2006/0222600 A1* | 10/2006 | Pinyayev | 424/49 |

FOREIGN PATENT DOCUMENTS

| | | |
|---|---|---|
| EP | 0927544 B1 | 10/1996 |
| GB | 2391462 A | 11/2004 |
| JP | 2002-517267 | 6/2002 |
| KR | 10-2005-54383 | 6/2005 |
| RU | 12509 U1 | 1/2000 |
| WO | WO 92/06671 | 4/1992 |
| WO | 9943387 A1 | 9/1999 |
| WO | WO 2004/030891 | 4/2004 |
| WO | WO 2005/096882 | 10/2005 |
| WO | WO 2005/099513 | 10/2005 |

* cited by examiner

LIGHT-EMITTING ORAL CARE IMPLEMENT

CROSS-REFERENCE TO RELATED APPLICATIONS

This application is a national stage entry under 35 U.S.C. §371 of International Patent Application No. PCT/US2006/060875, filed 14 Nov. 2006, which claims priority to U.S. Provisional Patent Application No. 60/736,250, filed 14 Nov. 2005, both of which are incorporated herein by reference.

FIELD OF THE INVENTION

The present invention relates to oral care implements in general, and more particularly to a method of forming a light-emitting toothbrush.

BACKGROUND

Toothbrushes are generally made in a method in which nylon bristled stock is anchored to a plastic toothbrush head via a metal staple. This requires a minimum head thickness of around 5 millimeters in order to reduce the possibility of plastic breakage during the stapling process given the tuft densities of most standard brushes. Furthermore, the toothbrush head and handle is generally molded in one step and it is a solid plastic part. This does not lend itself to placement of a light source in the toothbrush head.

In another well known process called in-mold tufting (IMT), nylon bristles are gathered and placed in an injection mold. Plastic is then injected around the bristles forming the toothbrush head and handle. The head must be large enough that plastic can flow over and around the "fused balls of nylon" commonly seen in these type of processes. The plastic over the fused balls retains the tuft in the brush during normal use. Once again there are generally no allowances made for insertion of a light source.

In each of these methods, incorporating a light source requires a post-processing step, such that the head must be made to accommodate a light source or the transmission of light from a source outside of the head. This post-processing requires time and resources, and often increases the cost to an unacceptable level. Or as an alternative, it requires making the head at a greater thickness (allowing for creation of a hollow section) increasing discomfort for the user while decreasing the user's ease of maneuverability. Accordingly, there is a need, therefore, for a practical, cost-efficient method of forming a light-emitting oral care implement, such as a toothbrush, that has an acceptable thickness and that is comfortable to the user.

Such need is met using a method of making an oral care implement or toothbrush where, for example, a head plate and handle are molded separately. The head plate is filled with cleaning elements such as nylon and the nylon is melted to an extremely thin "mat". Afterwards, this relatively thin head plate is ultrasonically welded to the handle. In this method there is an open cavity in the toothbrush head, or the toothbrush head is effectively hollow, allowing the opportunity to place light emitting elements or other items in the toothbrush head that may provide a therapeutic or cosmetic benefit. Included could be alarms or some other device that signal proper or improper brushing techniques, proper amount of brushing time, etc.

SUMMARY

An oral care implement, such as a toothbrush, comprises a head, a plurality of cleaning elements defined thereon, and a light source incorporated into or adjacent the head. The light source is incorporated into the implement prior to the incorporation of the cleaning elements for ease of manufacturing and a cost-effective, user-friendly assembly. The cleaning elements are preferably pre-formed and attached to the head after the light source so that the provision of the light source does not require any post-processing that might impair the integrity of the head or cleaning elements or unduly enlarge the head so that it is uncomfortable to the user.

DETAILED DESCRIPTION OF THE PREFERRED EMBODIMENTS

Figure 1:
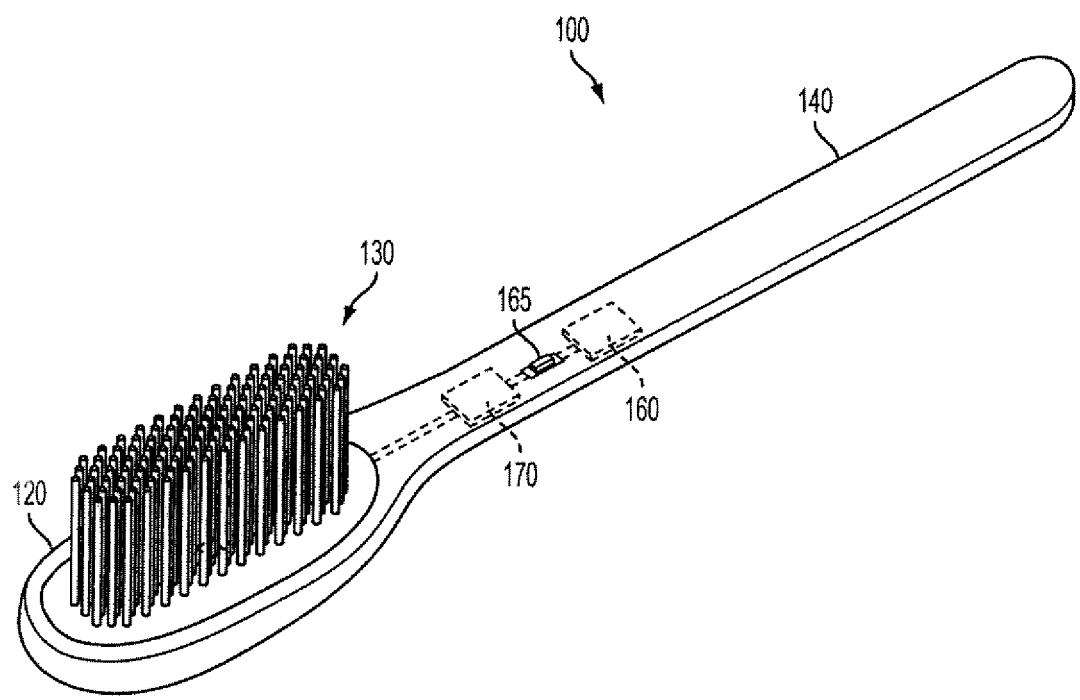
FIG. 1 is a schematic view of an oral care implement of the present invention.

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

FIG. 1 is a schematic view of an oral care implement 100 having a head 120 with a plurality of cleaning elements 130 provided thereon, and a handle 140 extending from the head 120. While the oral care implement 100 is illustrated as a toothbrush with non-movable cleaning elements (i.e., a so-called "manual" toothbrush), it will be understood that other oral care implements, such as "power" toothbrushes that have movable cleaning elements, flossers, tongue scrapers, or other implements that don't have cleaning elements, are contemplated. However, for purposes of convenience, the oral care implement 100 will be described as a toothbrush with cleaning elements 130. Furthermore, while the cleaning elements 130 are shown as conventional bristles or tufts of bristles, it will be understood that cleaning elements of any type (i.e., bristle tuft, bristle wall, elastomeric), material (i.e. nylon, elastomeric), size, cross-section (i.e., circular, rectangular, diamond-shaped) and the like will be contemplated.

Figure 2A:
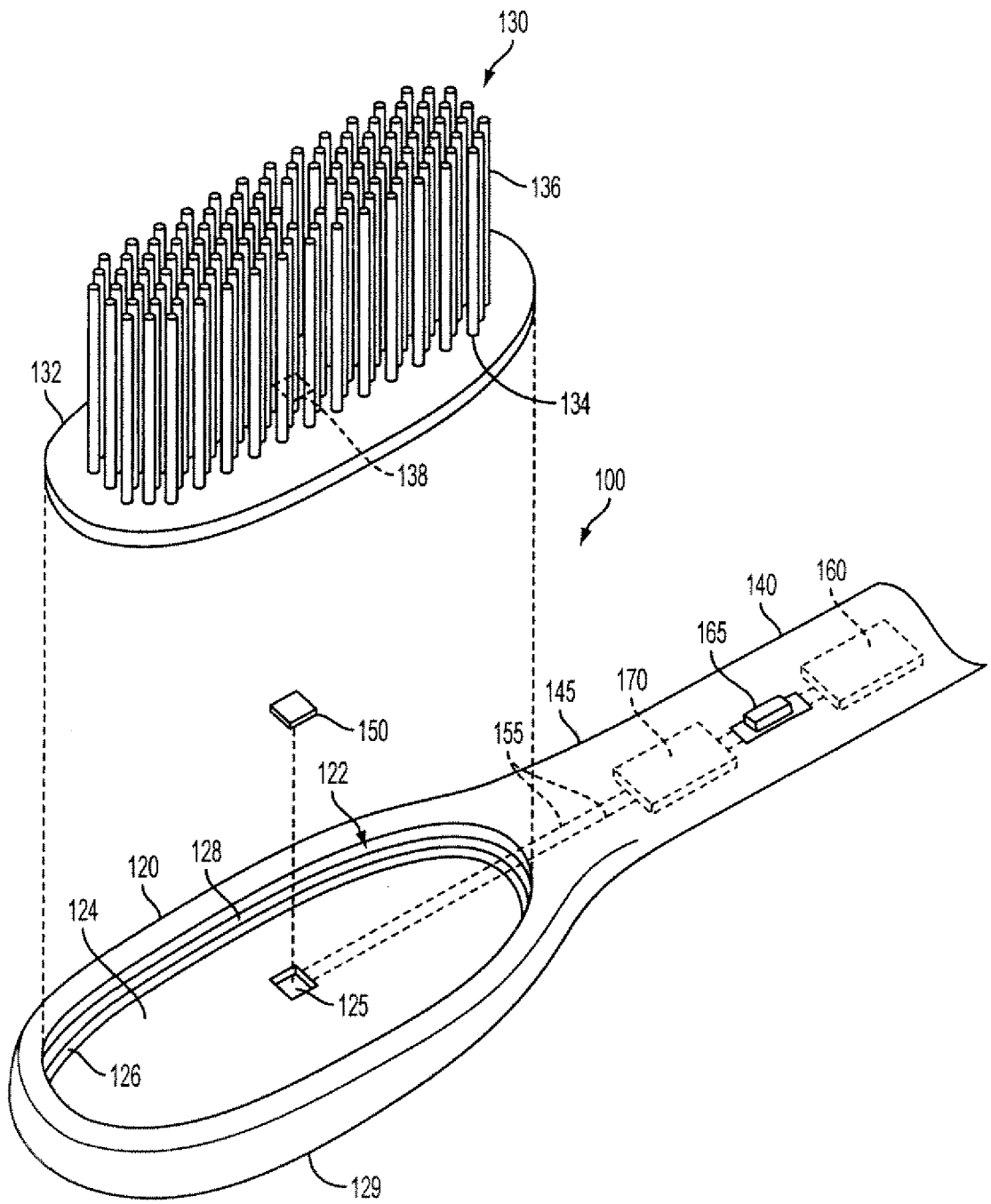
FIGS. 2A through 5B represent alternative embodiments of an oral care implement of the invention.

As shown in FIG. 2A, the head 120 is further provided with a chamber 122 having a floor 124 and a raised wall 126 having a lip 128. The raised wall 126 forms the side edges of the head 120, while the opposite side of the floor 124 defines the rear surface 129 of the head 120. The cleaning elements 130 are generally formed into a unitary structure that is secured to the head 120 by a process known in the art, such as by adhesion, ultrasonic welding, mechanical snap or press fit, and the like. In particular, the cleaning elements 130 are secured to a plate 132 that is seated on the lip 128. Such plate 132 is populated with separate cleaning elements 136 by traditional stapled tufting, or by so-called anchor-free tufting (AFT), wherein the ends 134 of a plurality of separate cleaning elements 136 are joined or fused together using a process known in the art. Other methods of forming the cleaning elements 130 known, such as in-mold tufting (IMT) could be utilized although this method may be less preferred in certain circumstances due to the probable increased size of the toothbrush head and the extra manufacturing steps involved. In this IMT method, a sandwich plate is made in which cleaning elements are embedded between two plastic faces that are made as thin as possible, with the cleaning elements extending from a front surface of the plate. Allowance could be made to attach a light source to the bottom or rear surface of this sandwich plate. This plate could then be joined to a handle by any known means such as ultrasonic welding, laser welding, adhesive, plastic overmolding, etc. Alternatively, the sandwich plate could be adhered to a pre-made handle in which the light source is mounted to the handle as described herein. The handle would then be designed in a way to provide mounting for the light source. Other manufacturing techniques known or to be developed are contemplated herein.

Provided in a socket 125 in the floor 124 of the head 120 of the embodiment of FIG. 2A is a light source 150 of any frequency or wavelength. Light source 150 is connected to a power source 160 provided in the handle 140 via connections 155 such as electrical wires or the like. Such power source 160 could take any form, such as, but not limited to, a hard-wired connection to a standard household electrical current, or a portable battery powered source that could be rechargeable, non-rechargeable, replaceable, non-replaceable, alkaline, nickel cadmium, lithium, polymeric, environmentally-friendly, solar etc. as desired.

Connections 155 are preferably routed through the neck 145 of the toothbrush 100, which neck 145 is defined by the region adjacent the head 120 between the head 120 and the handle 140. Passageways for the wiring connections 155 could be provided, for example, in a first molding and then covered with a second molding. The wiring 155 could also be covered with a second injection molded part that fits into the first molded part, could be covered by film, or in any number of other methods that would be obvious to one experienced in plastic goods manufacturing or in consumer goods packaging. A switch 165 may be provided in the handle 140 to activate the power source 160 and power the light source 150 to obtain oral care benefits as described below. Light emitted from the light source 150 is directed to the oral cavity through at least one opening 138 in the plate 132, which opening 138 defines a light passage between the chamber 122 and outside thereof Such opening 138 is preferably sealed to prevent invasion of water, bacteria and debris into the chamber 122.

The benefit of light emittance within an oral cavity include, but are not limited to, the increased ability of toothpaste active ingredients to penetrate areas of the oral cavity, particularly interproximal spaces, thus increasing the stated benefits of toothpaste in those areas with increased disruption of the plaque matrix. Generally, the light emittance could increase the plaque matrix disruption normally experienced with the act of brushing one's teeth. Light, with a high enough or specified frequency, can affect bacterial cells thus deleteriously affecting the ability of bacteria to generate within a plaque matrix further adding value towards a measurable, through expired volatiles, whole mouth clean experience. The presence of light might offer additional benefits, therapeutic value, in combination with specially formulated active ingredients or encapsulated active ingredients that the light would specifically actuate or catalyze offering synergistic affects in delivery vehicles as dentifrices or mouth rinses, or medicinal remedies which could offer relief from oral care health conditions, not all inclusive, such as xerostomia, cancerous lesions or abnormalities, sores, or post-operative maladies. In addition to the increased cleaning efficacy of the light, the user might experience sensory benefits such a cooling or heating effects, gingival or soft tissue stimulation or enhanced health, enamel polishing, enhanced desquamation, polishing, additional bacteriological affects on gram negative bacterial reduction, and an overall increased oral cavity cleansing perception.

Additionally, the present concept could be coupled with existing powered toothbrush motions including vibratory, oscillating, pulsating, revolving, sonic and ultrasonic as well as use in manual toothbrushes. The toothbrush could be designed with a specialized head section to vibrate or move at these specific frequencies to offer the light benefits to a full range of oral cavity regions. The method of action of the brush head should not be limited to vibration, but should be any type of activation that could involve a dentifrice or mouth rinse or oral care conditioning agent and toothbrush in combination where active ingredients are affected by the presence of light. Furthermore, the toothbrush head could also include either longitudinal or latitudinal serrations, splits, gaps, or designed separations throughout the supportive structure, which isolate functional regions of the toothbrush head, with each region capable of emitting light. Such separations include, but are not limited to, singular or multiplicative, and can be serpentine, straight lines, hinged, curves, diagonals, bisecting, symmetric or asymmetric, or other geometrically calculated or conceived configurations that allow for independent movement and/or cleaning action, of these isolated regions which upon the frontal surface of these independent action regions express non-shedding and shedding oral cavity tissue cleaning elements such as groupings or plurality of amide or non-amide filaments or elastomeric features or the like.

In addition, by pre-forming the cleaning elements 130 and assembling them over a pre-positioned light source, the manufacture of the toothbrush becomes more cost-effective and streamlined. Furthermore, the positioning and variation of the light source in the head chamber allows for flexibility in the type of light source, the type of cleaning elements and the manner in which the two are joined. This flexibility is not realized in prior art structures where the head is specifically designed to accommodate a specific light source in a specific location within a specific bristle construction.

Figure 2B:
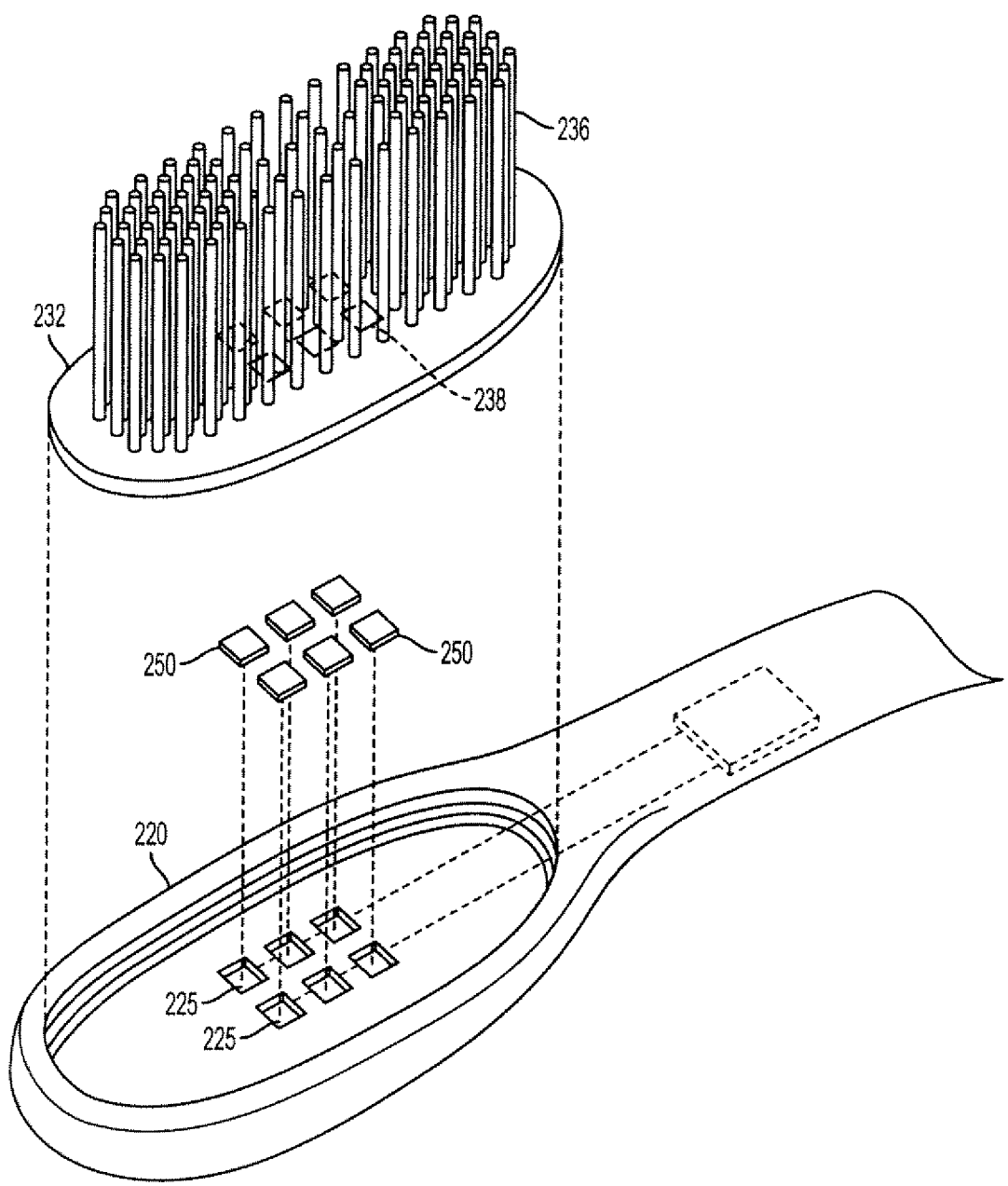
Figure 2C:
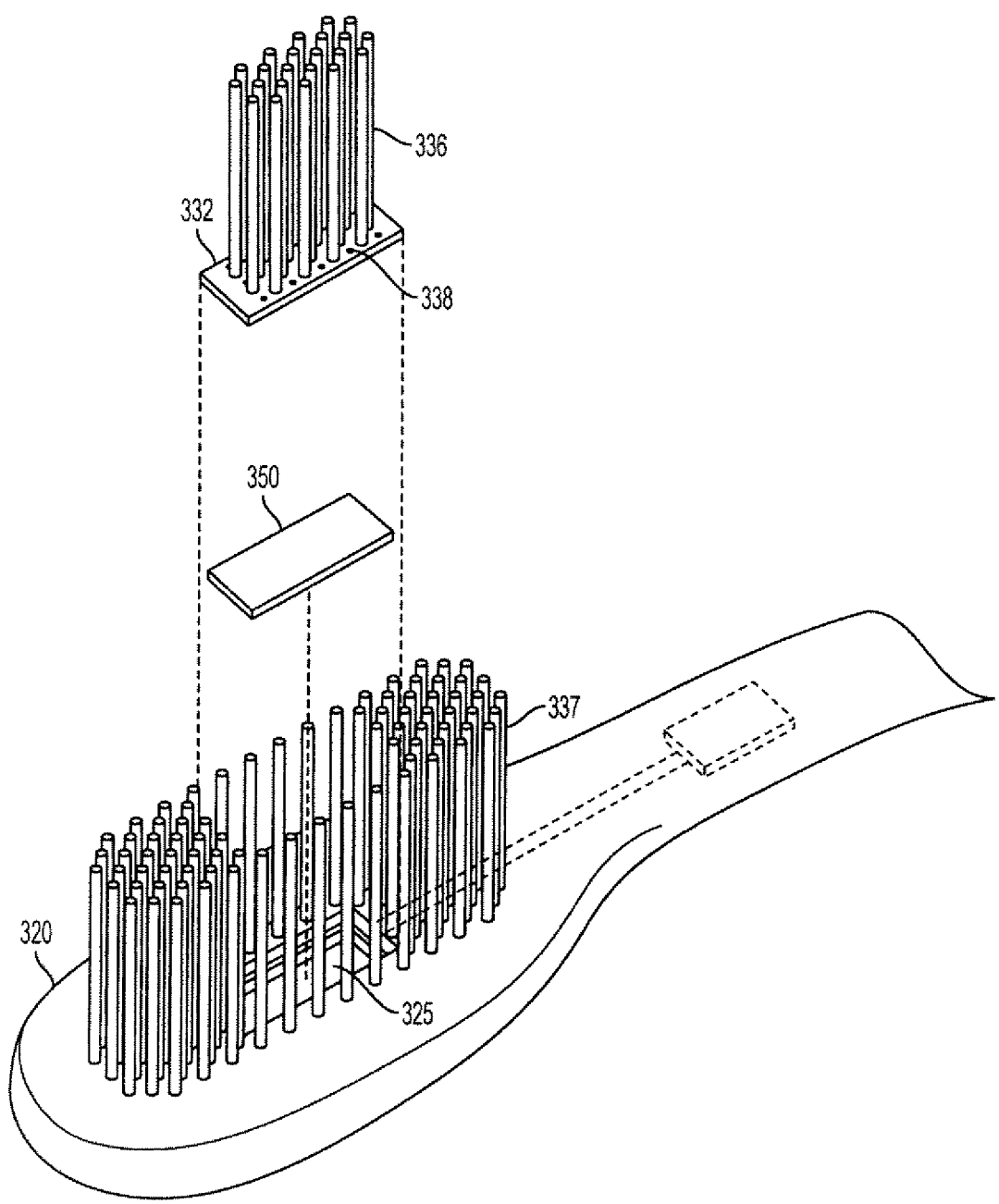
Figure 2D:
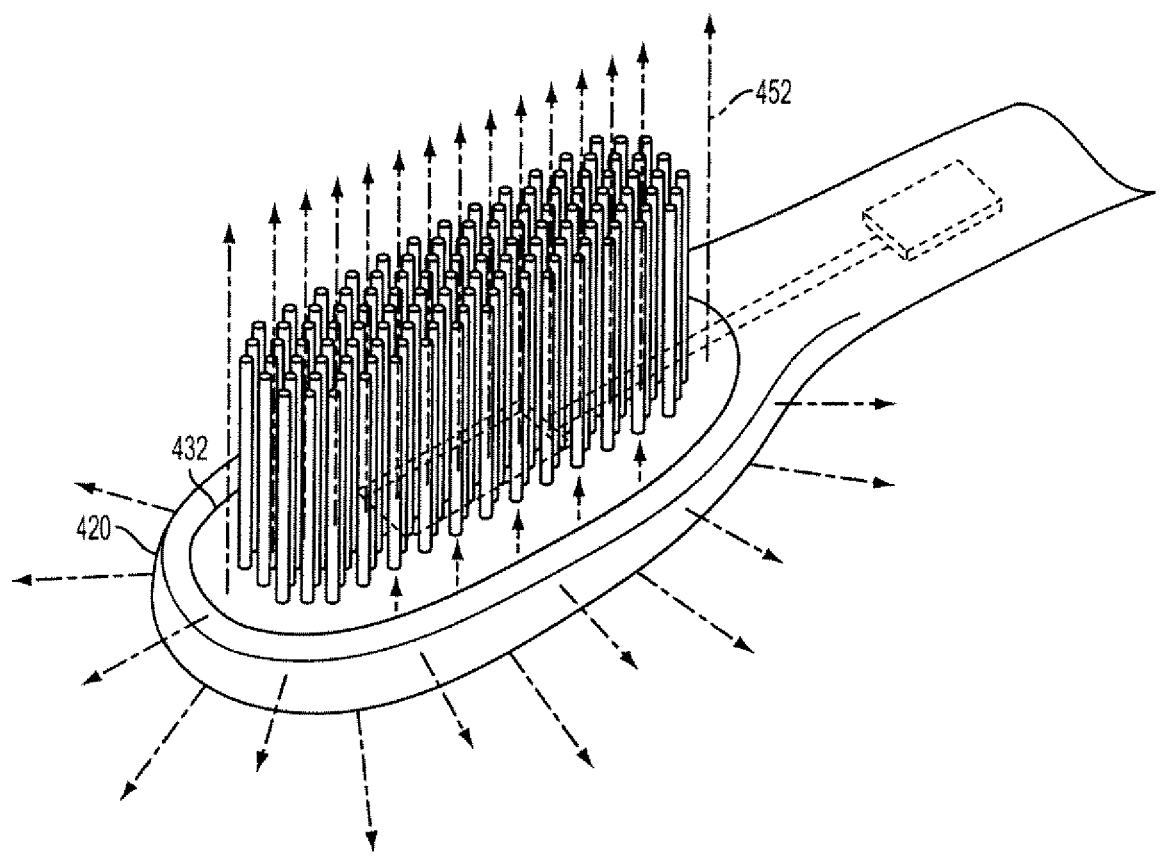

Light source 150 in FIG. 2A is shown as a square-shaped light emitting diode (LED) that is seated within a square-shaped socket 125. As used herein, the term LED is understood to include a variety of classes of LEDs such as, but not limited to, light-emitting organic materials or organic light-emitting polymers diodes (OLEDs), polymer light-emitting diodes (PLEDs), and light-emitting polymers (LEPs) which offer benefits regarding ease of manufacturing through flexible manufacturing techniques and design configurations, malleability, and that are environmental friendly, disposable and recyclable. Light source 150 could also be a surface-mounted device LED, an LED chip, or a non-LED based light source and/or could vary in shape, size and construction depending on the head environment. In the head 220 of the embodiment of FIG. 2B, a plurality of light sources 250 may be provided in a plurality of sockets 225 for emitting light through a plurality of openings 238 in a cleaning element plate 232. Alternatively, in the head 320 of the toothbrush of FIG. 2C, which also includes cleaning elements 337 fixed to the head 320, a single light source 350 may be provided in a single socket 325 for emitting light through a plurality of openings 338 in a cleaning element plate 332. In the embodiments of FIGS. 2A and 2B, the openings 138, 238 constitute focused light passages between the separate cleaning elements 136, 236, while in the embodiment of FIG. 2C, the openings 338 are uniformly interspersed among the separate cleaning elements 336 for a dispersed light passage and transmission. Such focused light passage is particularly evident if the plate 132, 232, 332 is made from a material that does not transmit light. However, as shown in the embodiment of FIG. 2D, if the head 420 and/or plate 432 is/are made from a material that transmits light (transparent or translucent for example), then the plate 432 may not require special openings or light passages as the light from the light source 450 could reach the oral cavity from a multitude of directions as shown by arrows 452.

Figure 3A:
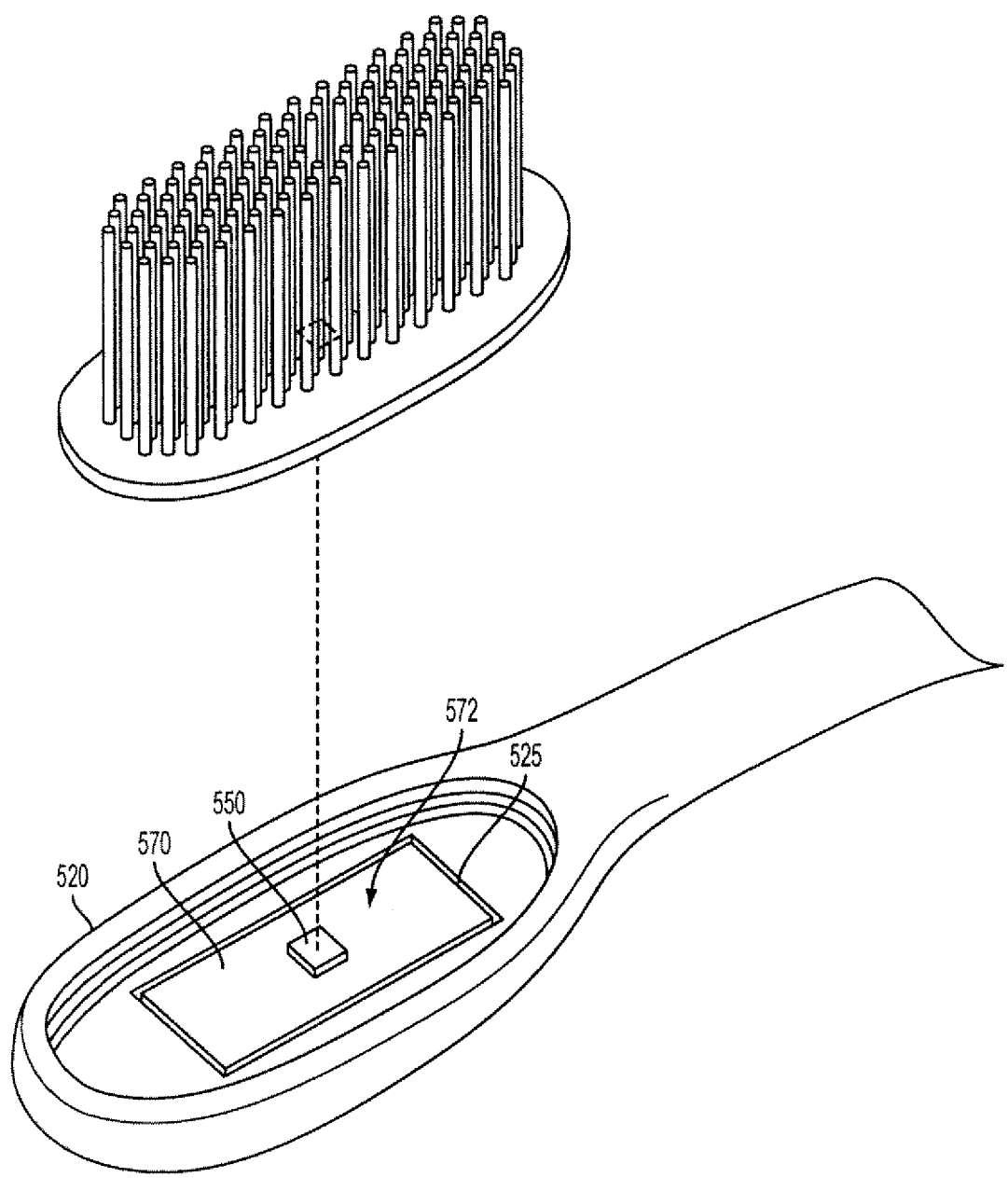
Figure 3B:
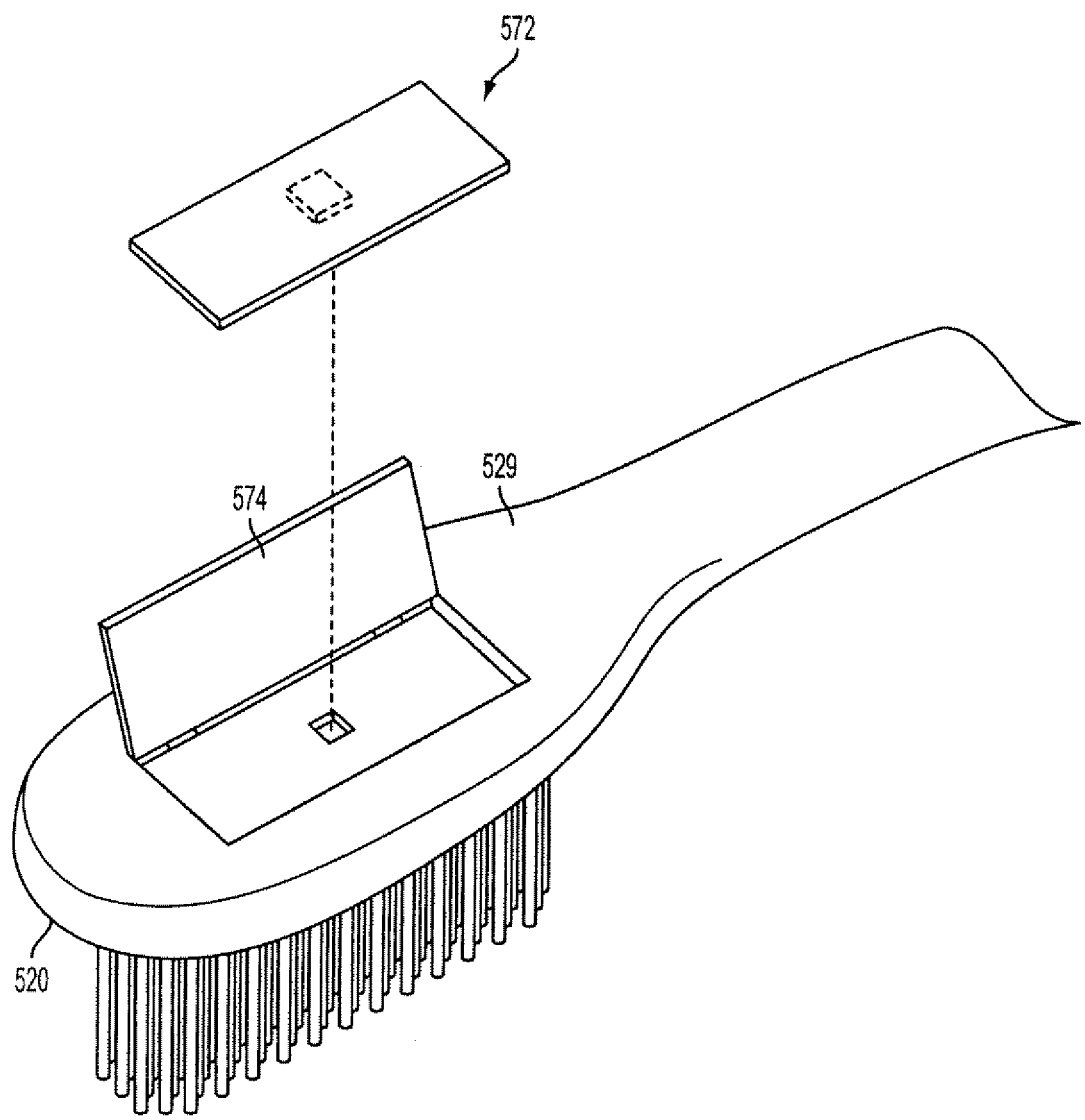
Figure 3C:
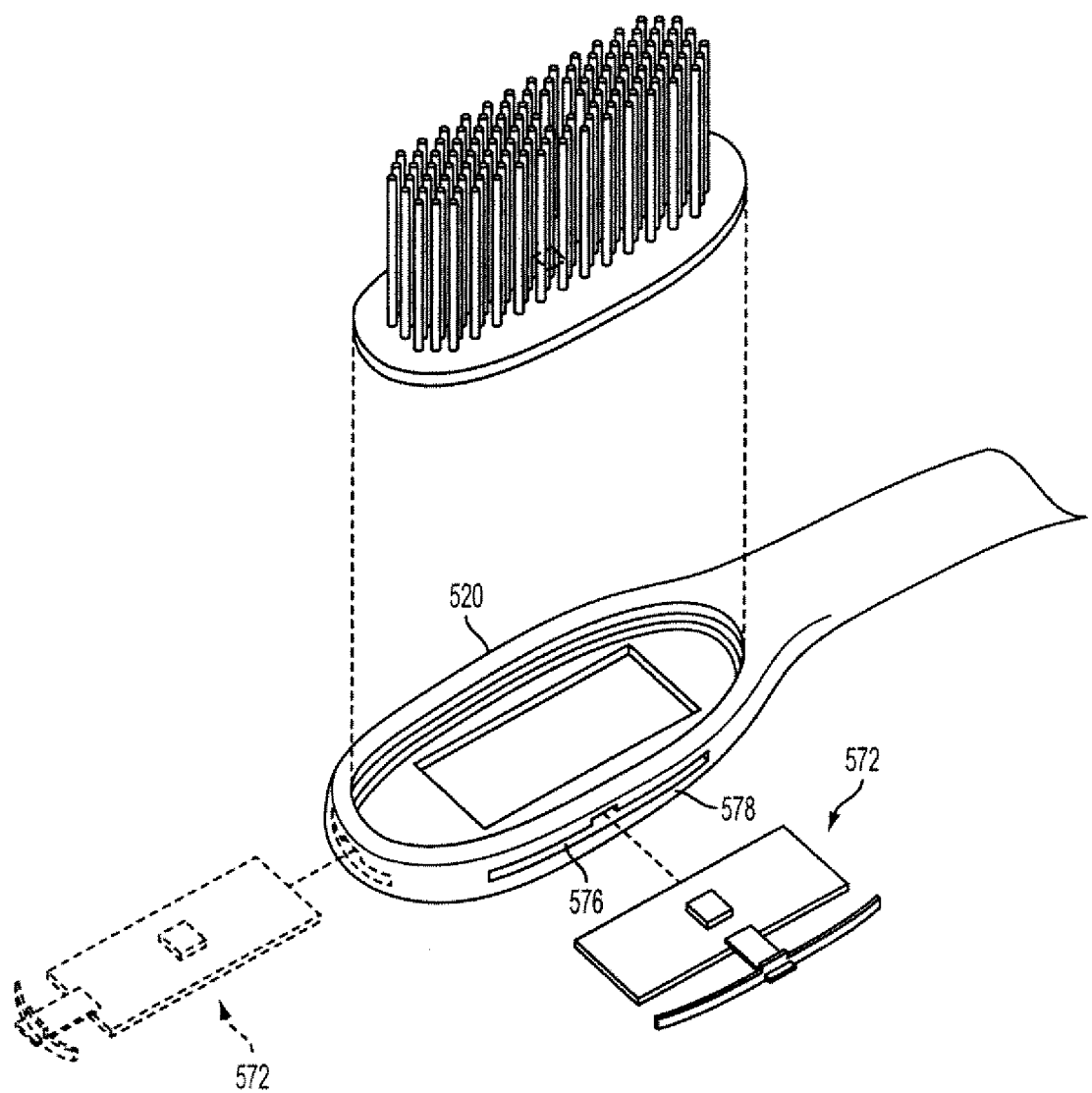

In the embodiments discussed above, the light source is connected to a power source in the handle. However, the power source may reside in other locations, such as the neck or the head. In addition, a control board 170 (FIG. 1) may be provided in the handle, for example, to control the operation of the light source based on the desired benefit. For example, it may be appropriate for certain situations to strobe the light source, or to have the light source emit light at only certain intervals for certain periods of time. In the embodiment of FIG. 3A, the light source 550 may reside on a control board 570 to form a controlled light assembly 572 that is itself seated in a socket 525 in the head 520. Such assembly could be non-removable as shown in FIG. 3A, or removable and replaceable via an access panel 574 (FIG. 3B) provided in the rear surface 529 in the head 520, or via an access slot 576 (FIG. 3C) provided along a side edge 578 or along an upper edge 579 of the head 520. It may be desirable to replace a light source if it burns out or malfunctions, or if a variety of light sources are desired at different times. For example, it may be preferable to use a first light source having a particular wavelength to treat a particular oral health condition, and then a second light source having a different wavelength to treat a different oral health condition, the two light sources being readily swapped or interchanged as desired.

Figure 4A:
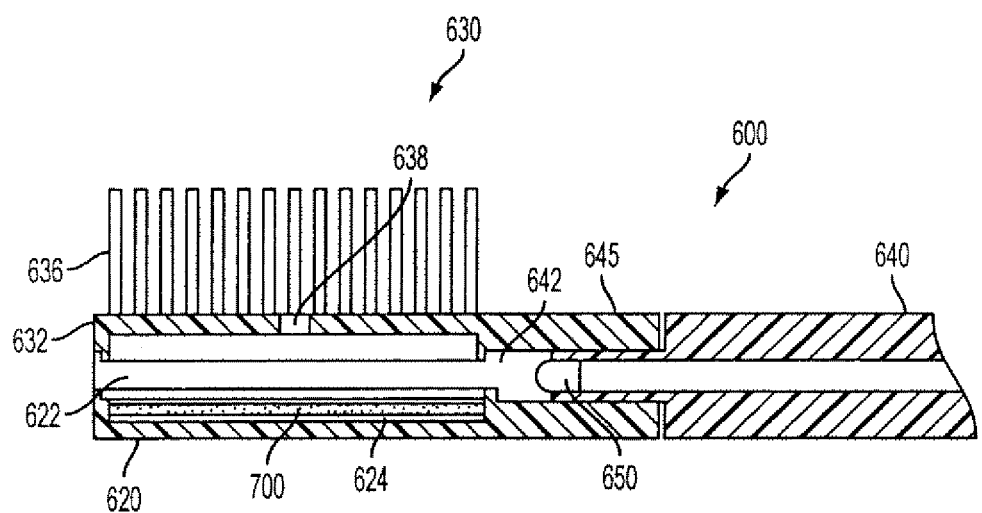
Figure 4B:
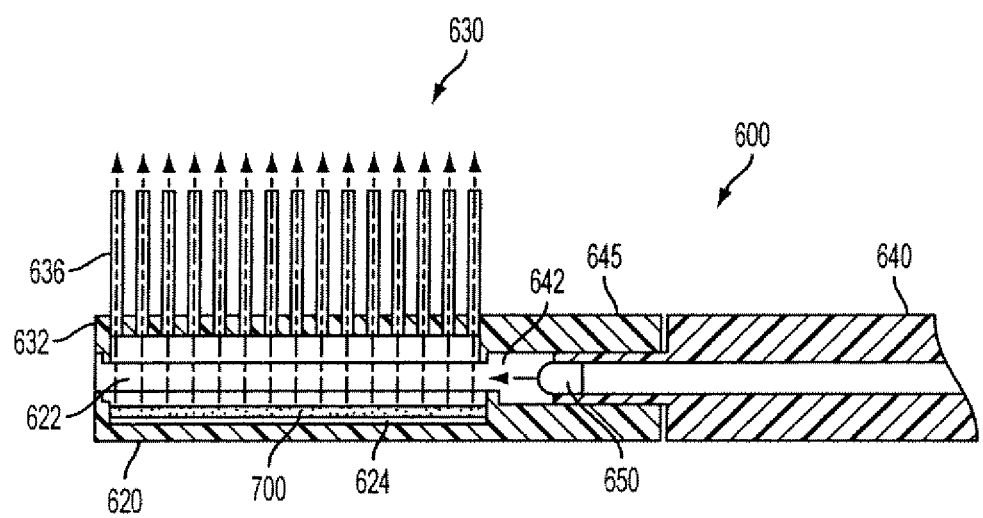

FIGS. 4A and 4B illustrate additional embodiments of a toothbrush 600 having a head 620 with cleaning elements 630 situated thereon and a handle 640. A light source 650 is located at the end 642 of the handle 640 adjacent the head 620, or in the neck 645 of the toothbrush 600, which light source 650 emits light into the chamber 622 defined between the floor 624 and head plate 632. As shown, the head plate 632 fits over the handle neck 645 and the brush assembly could be completed via ultrasonic welding as is currently done in the AFT technology. Alternatively, the head 620 could be removable from the neck 645 via a threaded connection or the like for replacement of the head 620 and/or access to the light source 650.

In the embodiments of FIGS. 4A and 4B, the floor 624 of the chamber 622 is lined with a reflective or refractive membrane 700 which allows light to be directed through the head plate 632 to the oral cavity as desired. This refractive or reflective membrane reorients the direction of light emitted, regardless of wavelength or frequency, and could be of any known material such as metallic, polymeric or a combination of materials. The membrane could be positioned parallel to the head plate 632 as shown, or at an angle thereto (not shown). The light may also be transmitted through the separate cleaning elements 636 anchored to the head plate 632 if such cleaning elements are made from suitable material. For example, if cleaning elements 636 are bristles, such bristles can be comprised of synthetic polyamides (nylons), polybutylene terephthalate, polyethylene terephthalate materials or elastomeric materials. Such bristles may or may not have incorporated within materials that enhance transference or transmittance of emitted light throughout or surrounding bristle material(s). Bristles may also consist of co-extruded materials and have various cross-sectional shapes or diameters for any of the aforementioned yet not all inclusive listing. The head plate 632 could also comprise specified geometric areas or regions 638, devoid of cleaning elements 636, to allow for light transference, which areas or regions 638 could also incorporated additional materials specific to enhancement of light transference, reflectance or refraction. For example, the areas or regions 638 could constitute openings that are covered by prisms or the like (not shown) that act in concert with the reflective or refractive properties of the membrane 700.

Figure 5A:
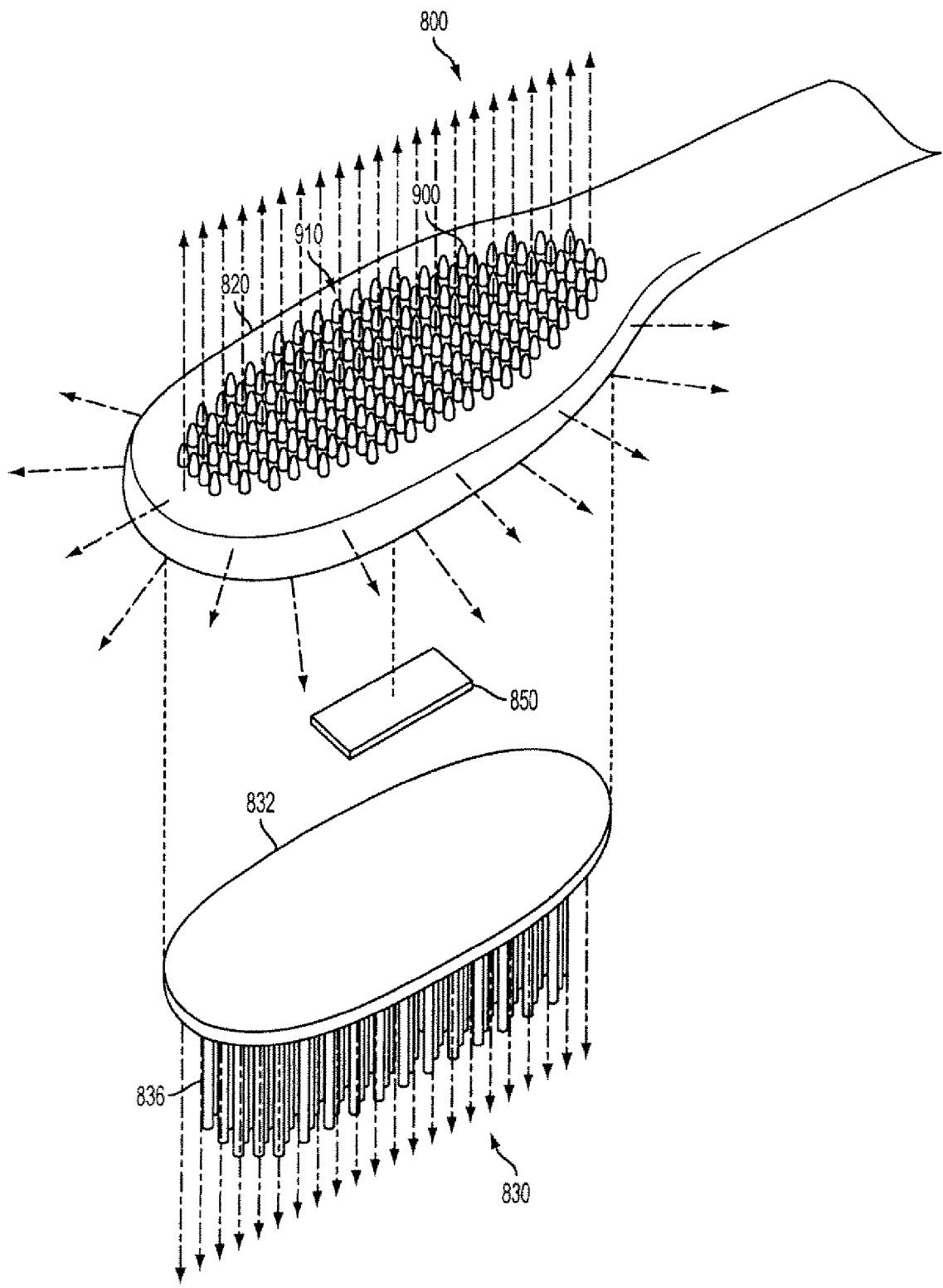
Figure 5B:
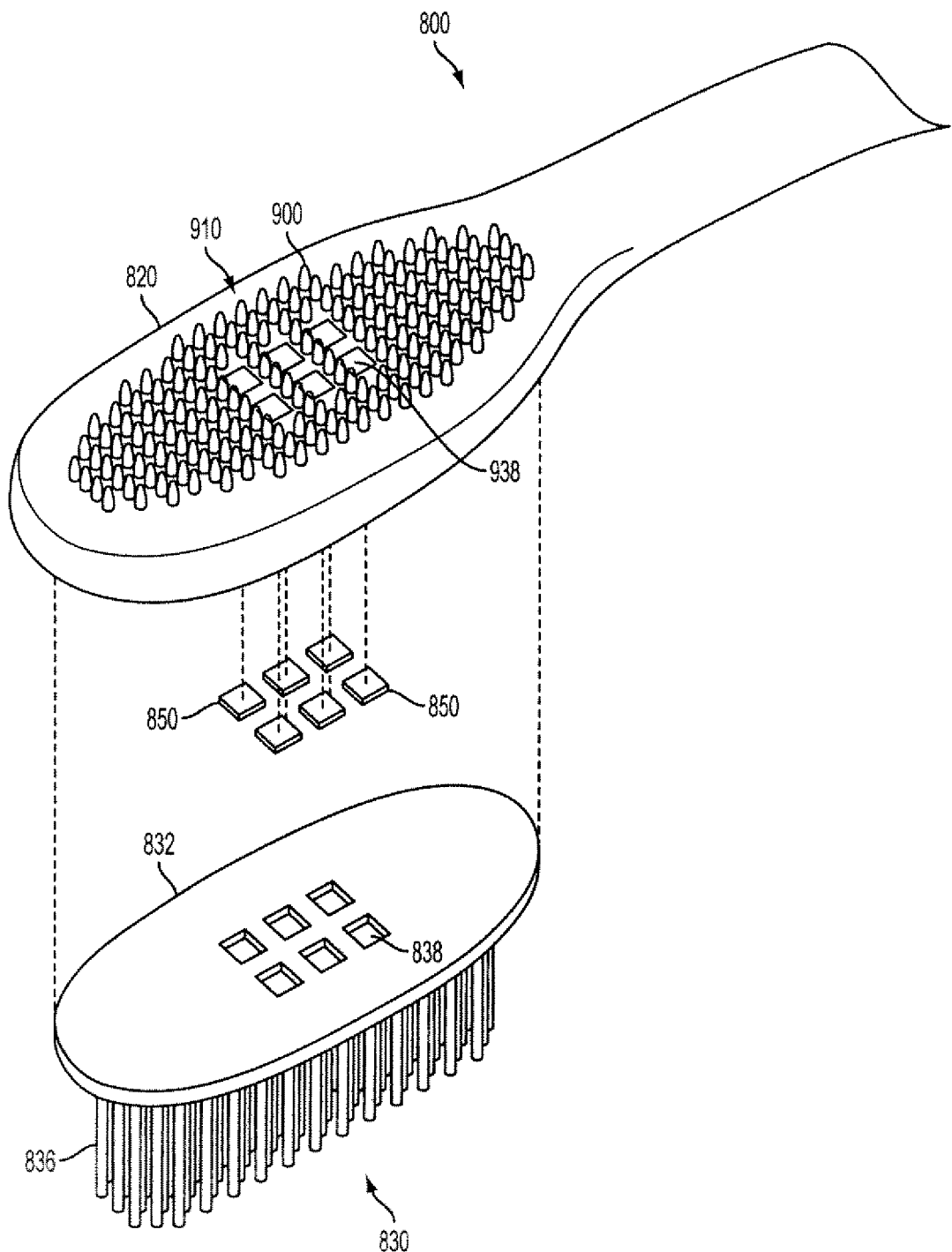

FIGS. 5A and 5B illustrate the head portion 820 of an additional embodiment of a toothbrush 800 having cleaning elements 830 on one side of the head 820 and a tongue or soft tissue cleaner 900 on the opposite side, with a light source 850 defined in or adjacent the head 820 as illustrated in previous embodiments. The soft tissue cleaner 900 may comprise a variety of configurations, such as a plurality of nubs 910 as described in U.S. application Ser. No. 10/869,922, which is incorporated by reference herein. In addition to, or instead of the transmission of light through the head plate 832, the soft tissue cleaner 900 may be formed of a light transmissive material, or it may comprise one or more light passages 938 similar in function to the light passages 838 through the head plate 832. Such passages 938 may be any shape or configuration as desired. Thus, the toothbrush 800 could direct light through two different cleaning element areas or regions on opposite sides of the head 820.

The tongue or soft tissue cleaning feature 900 may also incorporate products, such as sensates, medicaments, catalysts, active ingredients incompatible with active ingredients delivered through dentifrices, mouth rinses or oral care conditioning agents, sundry chemicals such as holistic ingredients, which offer sensorial relief for teething conditions and/or soft tissue irritation, antibacterial affects, cooling or tingling affects, fresh breath, tooth stain reduction, plaque or biofilm inhibition or a combination of aforementioned, which could alleviate or offer remedies towards oral cavity conditions for a period less than permanent.

What is claimed is:
1. A light-emitting oral care implement comprising:
  a) a head and a handle, the head further comprising a socket;
  b) a light source in or adjacent the head, the light source being removable and replaceable through an access panel on a rear surface of the head;
  c) a pre-formed plurality of cleaning elements secured to a plate that is positioned over the socket;
  d) a soft tissue cleaner on a side of the head opposite the cleaning elements;
  wherein the light source is defined between the cleaning elements and the socket; and
  wherein light from the light source transmits through the plate and through the soft tissue cleaner.
2. The implement of claim 1, the handle further comprising a power source for powering the light source.
3. The implement of claim 1, wherein the head further comprises a chamber, the plate positioned over the chamber, and wherein the socket is formed into a floor of the chamber, the light source being seated in the socket.
4. The implement of claim 1, further comprising at least one opening defined in the plate, the light from the light source transmitting through the opening,
5. The implement of claim 1, further comprising, a plurality of light passages formed in the plurality of cleaning elements.
6. The implement of claim 5, the head being formed of a light transmissive material such that light is transmitted through the head in addition to through the plurality of light passages.
7. The implement of claim 1, the head being formed of a light transmissive material for transmitting light from the light source.

8. A light-emitting oral care implement comprising:
a) a head and a handle, the head further comprising a socket;
b) a light source in or adjacent the head, the light source being, removable through a slot in an edge of the head, the slot forming a passageway from an external environment to the socket;
c) a pre-formed plurality of cleaning elements secured over the socket; and
wherein the light source is defined between the cleaning elements and the socket.

9. The implement of claim 8, where the slot is in an upper edge of the head.

10. The implement of claim 8, where the slot is in a side edge of the head.

11. The implement of claim 1, the light source being a light-emitting diode (LED).

12. The implement of claim 11, wherein the LED is a surface mounted device LED (SMD LED).

13. The implement of claim 1, the light source residing on a printed control board (PCB) in the head.

14. The implement of claim 13, the light source being a LED.

15. The implement of claim 14, the PCB being removable through the head.

16. The implement of claim 15, the PCB being removable through a rear surface of the head.

17. The implement of claim 1, wherein the light source is in the handle and the head emits light to a user's oral cavity during use of the oral care implement.

18. The implement of claim 1, wherein the plate is welded to the head.

19. The implement of claim 1, the soft tissue cleaner comprising, at least one light passage.

20. The implement of claim 1, the soft tissue cleaner conveying at least one benefit in addition to cleaning.

21. The implement of claim 1, the soft tissue cleaner being formed of a light transmissive material.

* * * * *